United States Patent
Wang et al.

(10) Patent No.: US 9,656,958 B2
(45) Date of Patent: May 23, 2017

(54) METHOD FOR SYNTHESIZING KEY INTERMEDIATE OF APIXABAN

(71) Applicants: SHANGHAI SYNCORES TECHNOLOGIES INC. LTD., Shanghai (CN); ZHEJIANG HUAHAI PHARMACEUTICAL CO., LTD., Zhejiang (CN)

(72) Inventors: Boyu Wang, Shanghai (CN); Jinfeng Yao, Shanghai (CN); Luning Huang, Shanghai (CN); Jeannie Zhang, Shanghai (CN)

(73) Assignees: Shanghai Syncores Technologies Inc. Ltd., Shanghai (CN); Zhejiang Huahai Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/902,286

(22) PCT Filed: Jul. 29, 2014

(86) PCT No.: PCT/CN2014/083228
§ 371 (c)(1),
(2) Date: Jan. 12, 2016

(87) PCT Pub. No.: WO2015/018289
PCT Pub. Date: Feb. 12, 2015

(65) Prior Publication Data
US 2016/0280646 A1  Sep. 29, 2016

(30) Foreign Application Priority Data
Aug. 2, 2013  (CN) .......................... 2013 1 0335663

(51) Int. Cl.
*C07D 211/02* (2006.01)
*C07D 211/40* (2006.01)
*C07D 211/88* (2006.01)
*C07D 211/76* (2006.01)

(52) U.S. Cl.
CPC .......... *C07D 211/88* (2013.01); *C07D 211/02* (2013.01); *C07D 211/40* (2013.01); *C07D 211/76* (2013.01)

(58) Field of Classification Search
CPC .... C07D 211/74; C07D 211/40; C07D 211/02
See application file for complete search history.

(56) References Cited

FOREIGN PATENT DOCUMENTS

| CN | 101967145 | 2/2011 |
|----|-----------|--------|
| CN | 103159670 | 6/2013 |
| WO | WO 2010/030983 | 3/2010 |

OTHER PUBLICATIONS

English translation of CN 101967145, published Feb. 9, 2011, p. 1-6.*
International Search Report for Application No. PCT/CN2014/083228, mailed Oct. 15, 2014.

* cited by examiner

*Primary Examiner* — Rebecca Anderson
*Assistant Examiner* — Karen Cheng
(74) *Attorney, Agent, or Firm* — Squire Patton Boggs (US) LLP

(57) ABSTRACT

The invention relates to a method for synthesizing an intermediate of Apixaban comprising reacting a compound of formula I with 5-chloro-valeryl chloride in the presence of inorganic base in an inert solvent to obtain a compound of formula II, with the reaction formula of (A), wherein R is selected from nitro group and the group (B). The method is mild in reaction condition, simple in operation, easy in purification, inexpensive in production cost, environmental-friendly, and suitable for industrial production.

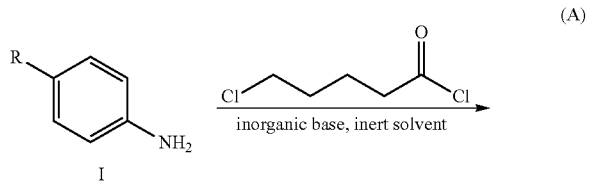

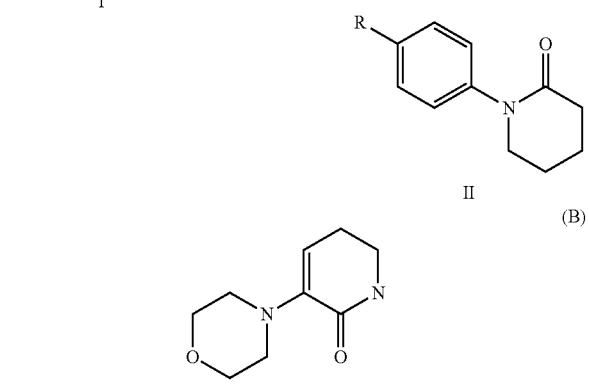

16 Claims, No Drawings

METHOD FOR SYNTHESIZING KEY INTERMEDIATE OF APIXABAN

The present application claims the priority of Chinese patent application No. 201310335663.4 filed on Aug. 5, 2013 before SIPO, entitled "Novel method for synthesizing key intermediate of Apixaban", which is incorporated herein by reference in its entirety.

FIELD OF THE INVENTION

The invention relates to a method for synthesizing an intermediate of Apixaban.

BACKGROUND

Apixaban, i.e., 1-(4-methoxylphenyl)-7-oxo-6-[4-(2-oxo-1-piperidyl)phenyl]-4,5,6,7-tetrahydro-1H-pyrazolo[3,4-c]pyridyl-3-carboxamide, has the following structural formula:

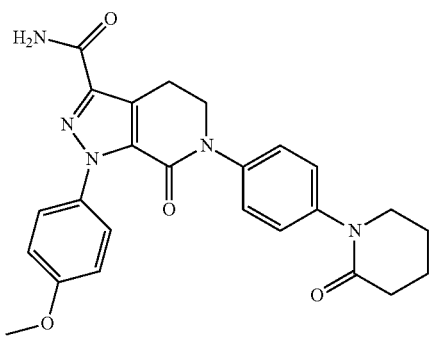 [SMILES: COc1ccc(-n2nc(C(N)=O)c3c2C(=O)N(c2ccc(N4CCCCC4=O)cc2)CC3)cc1]

Apixaban is an oral anticoagulant jointly developed by Pfizer and Squibb, acting as an inhibitor of Xa factor. Apixaban is now marketed in China, US and Europe. In China, it is approved for adult patients undergoing elective hip-joint or knee-joint replacement, and for preventing venous thrombus embolism (VTE). Its marketing provides a safe and effective new choice for anticoagulation after clinical orthopedic surgery, bringing out good news for the patients of elective hip-joint or knee-joint replacement in China. Clinical trials show that Apixaban has better effect than enoxaparin.

Each of 1-(4-nitrophenyl)piperidyl-2-one and 5,6-dihydro-3-(4-morpholinyl)-1-[4-(2-oxo-1-piperidyl)phenyl]-2(1H)-pyridone compounds is one of the key intermediates for synthesizing Apixaban, the relevant preparing methods of which are currently reported as follow:

1. CN publication No. CN101065379 discloses a method for preparing 1-(4-nitrophenyl)piperidyl-2-one comprising reacting paranitroaniline with 5-bromo-valeryl chloride in base through amidation and cyclization two steps reaction. The reaction scheme is as follow:

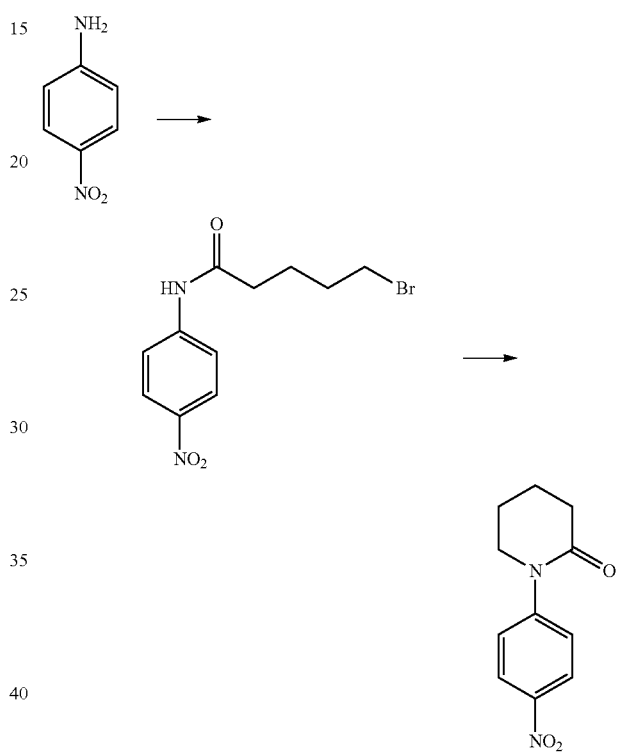

2. CN publication No. CN101967145 discloses a preparing method having the reaction scheme of:

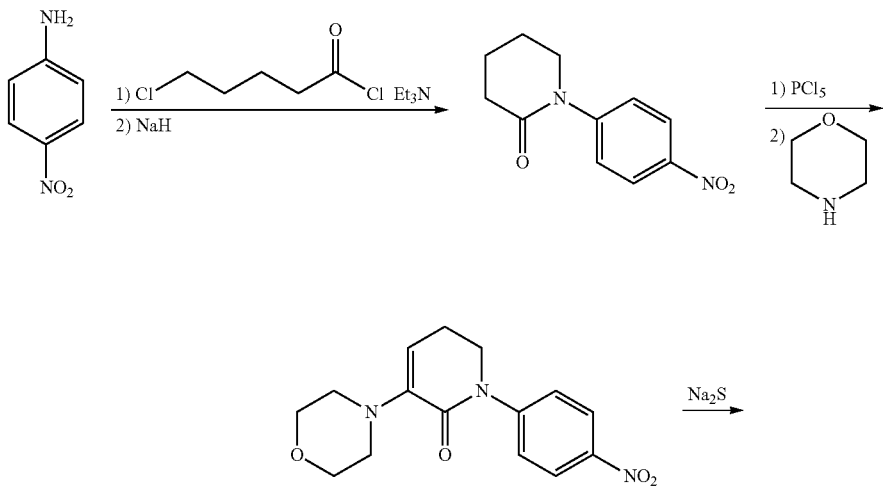

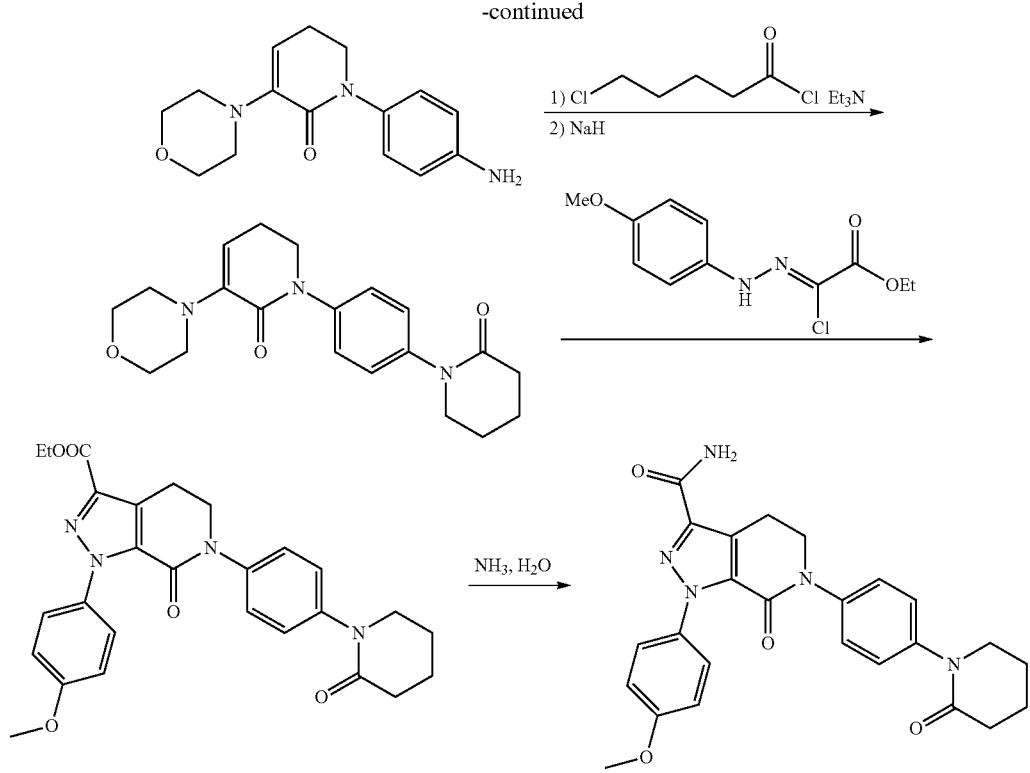

The primary problems suffered by these methods lie in that:
1) The quality control and preparation process is relatively difficult and the cost is relatively high because of using 5-bromo-valeryl chloride as raw material. Using organic base such as potassium tert-butoxide and the like as the base, and tetrahydrofuran as the solvent leads to the high cost, and thus they are not suitable for industrial production.
2) In the above reactions, the amidation reaction is carried out by a tertiary amine organic base of triethylamine and the cyclization reaction is carried out by a stronger base of sodium tert-butoxide, potassium tert-butoxide, or sodium hydride. These methods use very hazardous sodium hydride and have the disadvantages of complicated operations, tedious post-treatment and being relatively difficult quality control of product.

SUMMARY

An object of the invention is to provide a novel method for synthesizing key intermediate compound of Apixaban, overcoming the defects and deficiencies in the prior art.

The invention provides a method for synthesizing a compound of formula II—an intermediate compound of Apixaban, comprising the step of: reacting a compound of formula I with 5-chloro-valeryl chloride in an inert solvent in the presence of an inorganic base, with the reaction scheme of:

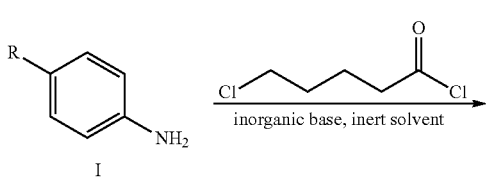

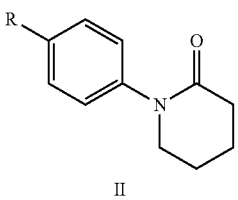

wherein, R is selected from nitro group and

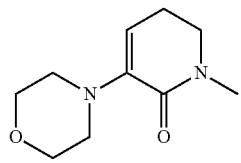

group.

The specific reaction scheme is as follows:

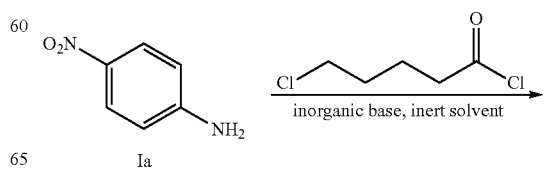

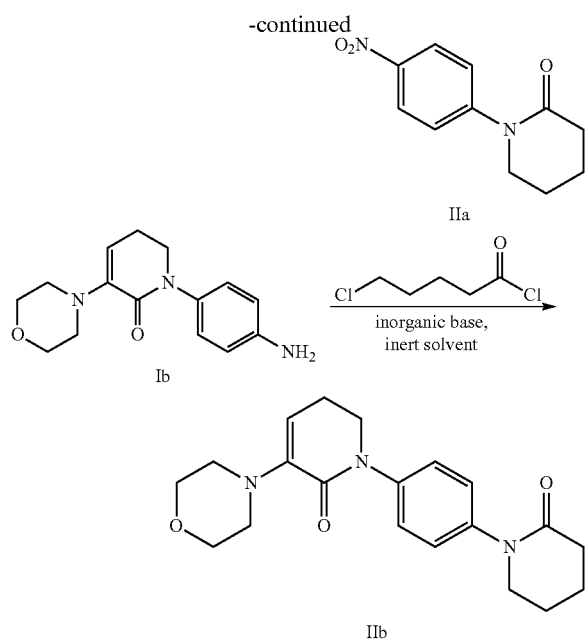

In the invention, 4-R-aniline and 5-chloro-valeryl chloride are reacted in an inert solvent in the presence of an inorganic base to obtain a compound of 1-(4-R-phenyl)piperidine-2-one.

The inorganic base used in the invention can be sodium hydroxide, potassium hydroxide, potassium carbonate, sodium carbonate, sodium bicarbonate, potassium bicarbonate, and the like, preferably sodium hydroxide.

The inert solvent used in the invention can be tetrahydrofuran, acetonitrile, dichloromethane, N,N-dimethylformamide, 1,2-dichloroethane, and the like, preferably acetonitrile.

In the invention, the compound of formula II (IIa or IIb) is preferably obtained by reacting 5-chloro-valeryl chloride with the compound of formula I (Ia or Ib) in the presence of sodium hydroxide in the solvent of acetonitrile, wherein the molar ratio of 5-chloro-valeryl chloride to the compound of formula I is 1.0-3.0, preferably 1.5-2.3; the molar ratio of sodium hydroxide to the compound of formula I is 2.0-10.0, preferably 5.0-6.5; the solvent is preferably acetonitrile, and the ratio of the volume of the solvent to the weight of the reactant is 25-40, preferably 28-35. In this case, the reaction temperature when dropwise adding 5-chloro-valeryl chloride is controlled to −10° C. to 10° C., preferably −5° C. to 5° C.

In the invention, the reaction temperature after completing the addition of 5-chloro-valeryl chloride is 0° C. to 50° C., preferably 15° C. to 40° C.

Moreover, the crude product of compound IIa can be recrystallized in a mixed solvent of ethyl acetate/petroleum ether (ethyl acetate/n-heptane and the like) in a ratio of ethyl acetate/petroleum ether of 2/1-1/1, preferably 1/1. The ratio of the volume of the recrystallization solvent to the weight of the crude product of compound IIa is 1-3, preferably 1-1.5.

The invention provides a method for synthesizing the intermediate of Apixaban without adding the organic base of tertiary amine, without using the expensive cyclization reagents of sodium tert-butoxide and potassium tert-butoxide, and without using the expensive and dangerous agent of sodium hydride. This method can obtain the intermediate of Apixaban by simply using inexpensive organic base via one pot process in an inert solvent. This method has the advantages of mild reaction condition, simple operation, being convenient for purification, low production cost, being environmentally friendly, and being suitable for industrial production.

DETAILED DESCRIPTION OF EMBODIMENTS

The technical solutions of the invention and the technical effects thereof will be further explained below in combination with examples, to more clearly illustrate the objects, technical features and effects of the invention.

EXAMPLE 1

Preparation of Compound IIa 5 g paranitroaniline and 150 ml acetonitrile were added into a 500 ml three-necked flask, stirred, and cooled to 0° C. in an ice bath. 8.7 g (6 eq) sodium hydroxide was added and stirred in the ice bath for 10 min. Then 9.4 ml of 5-chlorovaleryl chloride (2 eq) (diluted with 10 ml acetonitrile) was dropwise added while controlling the temperature to 0-5° C. After completing the addition, the content of the flask was stirred for 10 min while keeping the temperature. The temperature was naturally raised to 20° C. after removing the ice bath. The reaction was performed for 2 hours. After observing the absence of the reaction intermediate, the reaction solution was cooled to 0° C. in an ice bath, and adjusted to a neutral pH with 2 N of hydrochloric acid. The reaction solution was stood for layering. The resultant acetonitrile layer was concentrated to dryness, and washed with saturated sodium bicarbonate solution (30 ml*3) after adding 50 ml ethyl acetate. All the aqueous phases were combined, and then extracted with ethyl acetate. The resultant organic phases were combined, washed with saturated saline, dried, and concentrated to provide yellow solid containing parts of oil. The mixed solvent of ethyl acetate/petroleum ether (1:1, 8 ml) was added, heated to reflux, completely dissolved, stirred, naturally cooled to crystallize and filtered to obtain 6.64 g yellow solid. Yield: 83.2%. Purity: 99.0% (HPLC).

EI-MS (m/z): 220.1

HNMR (400 MHz, DMSO, ppm) δ: 8.24 (d, J=8.8 Hz, 2H), 7.63 (d, J=8.8 Hz, 2H), 3.71 (t, J=6.0 Hz, 2H), 2.48 (t, J=6.6 Hz, 2H), 1.84-1.91 (m, 4H).

EXAMPLE 2

Preparation of Compound IIa 5 g paranitroaniline and 150 ml dichloromethane were added into a 500 ml three-necked flask, stirred, and cooled to 0° C. in an ice bath. 8.7 g (6 eq) sodium hydroxide was added and stirred in the ice bath for 10 min. Then 9.4 ml 5-chloro-valeryl chloride (2 eq) (diluted with 10 ml dichloromethane) was dropwise added while controlling the temperature to 0-5° C. After completing the addition, the content of the flask was stirred for 10 min while keeping the temperature. The temperature was naturally raised to 30° C. after removing the ice bath. The reaction was performed for 2 to 6 hours. After observing the absence of the reaction intermediate, the reaction solution was cooled to 0° C. in an ice bath, and adjusted to a neutral pH with 2 N of hydrochloric acid. The reaction solution was stood for layering. The lower organic layer was washed with saturated sodium bicarbonate solution (30 ml*3), and concentrated to dryness to obtain yellow solid containing parts of oil. The mixed solvent of ethyl acetate/petroleum ether (1:1, 8 ml) was added, heated to reflux, completely dissolved, stirred, naturally cooled to crystallize and filtered to obtain 5.79 g yellow solid. Yield: 73.0%. Purity: 99.1%.

EXAMPLE 3

Preparation of Compound IIa 5 g paranitroaniline and 150 ml tetrahydrofuran were added into a 500 ml three-necked flask, stirred, and cooled to 0° C. in an ice bath. 8.7 g (6 eq) sodium hydroxide was added and stirred in the ice bath for 10 min. Then 9.4 ml 5-chloro-valeryl chloride (2 eq) (diluted with 10 ml tetrahydrofuran) was dropwise added while controlling the temperature to 0-5° C. After completing the addition, the content of the flask was stirred for 10 min while keeping the temperature. The temperature was naturally raised to 20° C. after removing the ice bath. The reaction was performed for 2 to 6 hours. After observing the absence of the reaction intermediate, the reaction solution was cooled to 0° C. in an ice bath, and adjusted to a neutral pH with 2 N of hydrochloric acid. The reaction solution was stood for layering. The organic layer was washed with saturated sodium bicarbonate solution (30 ml*3), and concentrated to dryness to obtain yellow solid containing parts of oily. The mixed solvent of ethyl acetate/petroleum ether (1:1, 8 ml) was added, heated to reflux, completely dissolved, stirred, naturally cooled to crystallize and filtered to obtain 4.78 g yellow solid. Yield: 60.0%. Purity: 98.3%.

EXAMPLE 4

Preparation of Compound IIa 5 g paranitroaniline and 150 ml acetonitrile were added into a 500 ml three-necked flask, stirred, and cooled to 0° C. in an ice bath. 8.1 g (4 eq) potassium hydroxide was added and stirred in the ice bath for 10 min. Then 10.8 ml of 5-chloro-valeryl chloride (2.3 eq) (diluted with 10 ml acetonitrile) was dropwise added while controlling the temperature to 0-5° C. After completing the addition, the content of the flask was stirred for 10 min while keeping the temperature. The temperature was naturally raised to 20° C. after removing the ice bath. The reaction was performed for 2 to 4 hours. After observing the absence of the reaction intermediate, the reaction solution was cooled to 0° C. in an ice bath, and adjusted to a neutral pH with 2 N of hydrochloric acid. The reaction solution was stood for layering. The acetonitrile layer was concentrated to dryness, and washed with saturated sodium bicarbonate solution (30 ml*3) after adding 50 ml ethyl acetate. All the aqueous phases were combined, and extracted with ethyl acetate. The organic phases were combined, washed with saturated saline, dried, and concentrated to provide yellow solid containing parts of oil. The mixed solvent of ethyl acetate/petroleum ether (1:1, 8 ml) was added, heated to reflux, completely dissolved, stirred, naturally cooled to crystallize and filtered to provide 5.53 g yellow solid. Yield: 69.3%. Purity: 98.9%.

EXAMPLE 5

Preparation of Compound IIb 2 g compound C (compound Ib) and 50 ml acetonitrile were added into a three-necked flask to obtain a turbid solution. The turbid solution was stirred and cooled to 0° C. in an ice bath. 1.75 g (6 eq) sodium hydroxide was added and stirred in the ice bath for 10 min. Then 1.9 ml of 5-chloro-valeryl chloride (2 eq) (diluted with 2 ml acetonitrile) was dropwise added while controlling the temperature to 0-5° C. After completing the addition, the ice bath was removed and the temperature was naturally raised to 30° C. The reaction was performed for 5 hours. After observing the absence of the starting material and the intermediate state of the reaction, the reaction solution was cooled to 0° C. in an ice bath, and adjusted to a neutral pH with 6 N of hydrochloric acid. The reaction solution was concentrated to dryness, pulpifying for 1 hour after adding 8 ml saturated sodium bicarbonate solution, and filtered to obtain 2.29 g yellow solid. Yield: 87.5%. Purity: 95.3% (HPLC).

EI-MS (m/z): 355.2

HNMR (400 MHz, DMSO, ppm) δ7.32 (d, J=8.8 Hz, 2H), 7.26 (d, J=8.8 Hz, 2H), 5.71 (t, J=4.8 Hz, 1H), 3.72-3.69 (m, 2H), 3.65-3.63 (m, 4H), 3.60-3.57 (m, 2H), 2.79-2.77 (m, 4H), 2.44-2.41 (m, 2H), 2.40-2.39 (m, 2H), 1.88-1.82 (m, 4H).

EXAMPLE 6

Preparation of Compound IIb 2 g compound C (compound Ib) and 60 ml dichloromethane were added into a three-necked flask, stirred, and cooled to 0° C. in an ice bath. 1.75 g (6 eq) sodium hydroxide was added and stirred in the ice bath for 10 min. Then 1.9 ml 5-chloro-valeryl chloride (2 eq) (diluted with 2 ml dichloromethane) was dropwise added while controlling the temperature to 0-5° C. After completing the addition, the ice bath was removed and the temperature was naturally raised to 25° C. The reaction was performed for 5 hours. After observing the absence of the starting material and the intermediate state of the reaction, the reaction solution was cooled to 0° C. in an ice bath, and adjusted to a neutral pH with 6 N of hydrochloric acid to layer. The aqueous layer was extracted with 30 ml dichloromethane. The organic phase was concentrated to dryness, pulpifying for 1 hour after adding 8 ml saturated sodium bicarbonate solution and filtered to obtain 2.0 g yellow solid. Yield: 77.3%. Purity: 96.0%.

EXAMPLE 7

Preparation of Compound IIb 2 g compound C (compound Ib) and 60 ml tetrahydrofuran were added into a three-necked flask, stirred, and cooled to 0° C. in an ice bath. 1.75 g (6 eq) sodium hydroxide was added and stirred in the ice bath for 10 min. Then 1.9 ml 5-chloro-valeryl chloride (2 eq) (diluted with 2 ml dichloromethane) was dropwise added while controlling the temperature to 0-5° C. After completing the addition, the ice bath was removed and the temperature was naturally raised to 25° C. The reaction was performed for 4 hours. After observing the absence of the starting material and the intermediate state of the reaction, the reaction solution was cooled to 0° C. in an ice bath, and adjusted to a neutral pH with 6 N of hydrochloric acid to layer. The aqueous layer was extracted with 30 ml dichloromethane. The organic phase was concentrated to dryness, pulpifying for 1 hour after adding 8 ml saturated sodium bicarbonate solution and filtered to obtain 1.89 g yellow solid. Yield: 72.3%. Purity: 94.9%.

EXAMPLE 8

Preparation of Compound IIb 2 g compound C (compound Ib) and 60 ml acetonitrile were added into a three-necked flask, stirred, and cooled to 0° C. in an ice bath. 4.62 g (6 eq) sodium carbonate was added and stirred in the ice bath for 10 min. Then 2.2 ml 5-chloro-valeryl chloride (2.3 eq) (diluted with 3 ml acetonitrile) was dropwise added while controlling the temperature to 0-5° C. After completing the addition, the ice bath was removed and the temperature was naturally raised to 30° C. The reaction was performed for 20 hours. After observing the completion of the reaction, the reaction solution was cooled to 0° C. in an ice bath, and adjusted to a neutral pH with 6 N of hydrochloric acid. The reaction solution was concentrated to dryness, pulpifying for 1 hour after adding 16 ml saturated sodium bicarbonate solution, and filtered to obtain 1.76 g yellow solid. Yield: 67.3%. Purity: 95.0%.

The invention claimed is:

1. A method for synthesizing an intermediate of Apixaban of formula II, characterized in that, the method comprises the step of: reacting a compound of formula I with 5-chloro-valeryl chloride in an inert solvent in the presence of an inorganic base to obtain a compound of formula II, with the reaction scheme of:

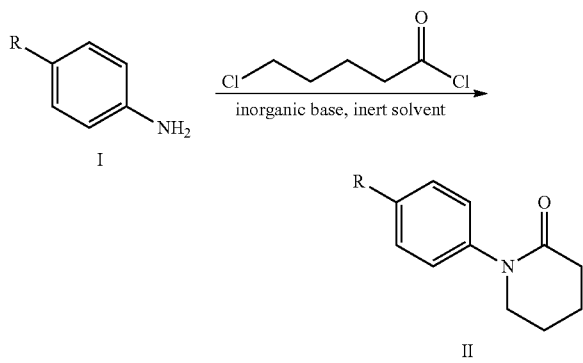

wherein R is selected from nitro group or

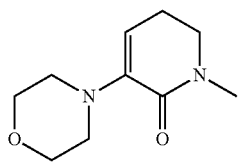

group;

the inorganic base is selected from the group consisting of sodium hydroxide, potassium hydroxide, sodium carbonate, potassium carbonate, sodium bicarbonate, or potassium bicarbonate.

2. The method according to claim 1, characterized in that, the inert solvent is selected from the group consisting of tetrahydrofuran, acetonitrile, dichloromethane, N,N-dimethylformamide, or 1,2-dichloroethane.

3. The method according to claim 1, characterized in that, the inorganic base is sodium hydroxide.

4. The method according to claim 1, characterized in that, the inert solvent is acetonitrile.

5. The method according to claim 1, characterized in that, the molar ratio of 5-chloro-valeryl chloride to the compound of formula I is 1.0 -3.0:1.

6. The method according to claim 1, characterized in that, the inorganic base is sodium hydroxide, and the molar ratio of sodium hydroxide to the compound of formula I is 2.0 - 10.0:1.

7. The method according to claim 1, characterized in that, the inert solvent is acetonitrile, and the ratio of the volume of the solvent to the weight of the reactant is 25 - 40:1.

8. The method according to claim 1, wherein 5-chloro-valeryl chloride is added dropwise, and the reaction temperature when dropwise adding 5-chloro-valeryl chloride is controlled to -10° C. to 10° C.

9. The method according to claim 1, wherein 5-chloro-valeryl chloride is added dropwise, and the reaction temperature after completing the addition of 5-chloro-valeryl chloride is 0° C. to 50° C.

10. The method according to claim 2, characterized in that, the inert solvent is acetonitrile.

11. The method according to claim 5, characterized in that, the molar ratio of 5-chloro-valeryl chloride to the compound of formula I is 1.5 -2.3:1.

12. The method according to claim 6, characterized in that, the molar ratio of sodium hydroxide to the compound of formula I is 5.0 - 6.5:1.

13. The method according to claim 7, characterized in that, the ratio of the volume of the solvent to the weight of the reactant is 28 - 35:1.

14. The method according to claim 2, characterized in that, the inert solvent is acetonitrile, and the ratio of the volume of the solvent to the weight of the reactant is 25 - 40:1.

15. The method according to claim 8, wherein the reaction temperature when dropwise adding 5-chloro-valeryl chloride is controlled to -5° C. to 5° C.

16. The method according to claim 9, wherein the reaction temperature after completing the addition of 5-chloro-valeryl chloride is 15° C. to 40° C.

* * * * *